United States Patent
Lee

(10) Patent No.: US 9,308,373 B2
(45) Date of Patent: Apr. 12, 2016

(54) ARCHITECTURES FOR SHARING OF CURRENT SOURCES IN AN IMPLANTABLE MEDICAL DEVICE

(75) Inventor: Dongchul Lee, Agua Dulce, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 119 days.

(21) Appl. No.: 13/485,416

(22) Filed: May 31, 2012

(65) Prior Publication Data

US 2013/0006315 A1    Jan. 3, 2013

Related U.S. Application Data

(60) Provisional application No. 61/502,409, filed on Jun. 29, 2011.

(51) Int. Cl.
*A61N 1/36* (2006.01)
*A61N 1/372* (2006.01)

(52) U.S. Cl.
CPC ........ *A61N 1/36185* (2013.01); *A61N 1/36125* (2013.01); *A61N 1/372* (2013.01)

(58) Field of Classification Search
CPC ................... A61N 1/36125; A61N 1/36128
See application file for complete search history.

(56) References Cited

U.S. PATENT DOCUMENTS

| | | | |
|---|---|---|---|
| 4,628,934 A | 12/1986 | Pohndorf et al. | |
| 5,344,429 A | 9/1994 | Smits | |
| 5,470,341 A | 11/1995 | Kuehn et al. | |
| 5,522,865 A * | 6/1996 | Schulman | A61N 1/36032 607/32 |
| 5,757,167 A | 5/1998 | Arora et al. | |
| 6,038,477 A | 3/2000 | Kayyali | |
| 6,181,969 B1 | 1/2001 | Gord | |
| 6,473,653 B1 | 10/2002 | Schallhorn et al. | |
| 6,516,227 B1 * | 2/2003 | Meadows et al. | ............... 607/46 |
| 6,895,280 B2 | 5/2005 | Meadows et al. | |
| 7,024,246 B2 | 4/2006 | Acosta et al. | |
| 7,127,298 B1 | 10/2006 | He et al. | |
| 2003/0093130 A1 | 5/2003 | Stypulkowski | |
| 2007/0038250 A1 | 2/2007 | He et al. | |
| 2007/0100399 A1 | 5/2007 | Parramon et al. | |
| 2007/0293914 A1 | 12/2007 | Woods et al. | |
| 2009/0259278 A1 | 10/2009 | Torgerson et al. | |
| 2010/0042187 A1 | 2/2010 | Werder et al. | |
| 2011/0125223 A1 | 5/2011 | Carbunaru et al. | |

FOREIGN PATENT DOCUMENTS

| | | |
|---|---|---|
| EP | 1449561 | 8/2004 |
| WO | 2010019867 | 2/2010 |

OTHER PUBLICATIONS

International Search Report and Written Opinion regarding corresponding PCT application No. PCT/US2012/041326, dated Oct. 17, 2012.

* cited by examiner

*Primary Examiner* — Eric D. Bertram
(74) *Attorney, Agent, or Firm* — Lewis, Reese & Nesmith, PLLC

(57) ABSTRACT

A group select matrix is added to an implantable stimulator device to allow current sources to be dedicated to particular groups of electrodes at a given time. The group select matrix can time multiplex the current sources to the different groups of electrodes to allow therapy pulses to be delivered at the various groups of electrodes in an interleaved fashion. Each of the groups of electrodes may be confined to a particular electrode array implantable at a particular non-overlapping location in a patient's body. A switch matrix can be used in conjunction with the group select matrix to provide further flexibility to couple the current sources to any of the electrodes.

14 Claims, 11 Drawing Sheets

US 9,308,373 B2

ARCHITECTURES FOR SHARING OF CURRENT SOURCES IN AN IMPLANTABLE MEDICAL DEVICE

CROSS REFERENCE TO RELATED APPLICATIONS

This is a non-provisional of U.S. Provisional Application Ser. No. 61/502,409, filed Jun. 29, 2011, which is incorporated herein by reference, and to which priority is claimed.

FIELD OF THE INVENTION

The present invention relates generally to implantable medical devices, and more particularly to improved current source architectures for an implantable neurostimulator.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc.

FIGS. 1A and 1B shows a traditional Implantable Pulse Generator (IPG) 100, which includes a biocompatible device case 30 formed of a conductive material such as titanium for example. The case 30 typically holds the circuitry and a battery necessary for the IPG 100 to function, although IPGs can also be powered via external RF energy and without a battery. The IPG 100 includes in this simple example an electrode array 102 containing a linear arrangement of electrodes 106. The electrodes 106 are carried on a flexible body 108, which also houses the individual electrode leads 112 coupled to each electrode. In the illustrated embodiment, there are eight electrodes on array 102, labeled $E_1$-$E_8$, although the number of electrodes is application specific and therefore can vary. Array 102 couples to case 30 using a lead connector 38, which is fixed in a non-conductive header material 36 such as epoxy for example. As is well known, the array 102 is implanted in an appropriate location in a patient to provide suitable simulative therapy, and is coupled through the patient's tissue to the IPG 100, which may be implanted somewhat distant from the location of the array.

As shown in FIG. 1B, the IPG 100 typically includes an electronic substrate assembly 14 including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transcutaneously transmit/receive data to/from an external controller (not shown); and a charging coil 18 for transcutaneously charging or recharging the IPG's battery 26 using an external charger (also not shown).

A portion of circuitry 20 in the IPG 100 is dedicated to the provision of therapeutic currents to the electrodes 106. Such currents are typically provided by current sources 150, as shown in FIGS. 2A and 2B. In many current-source based architectures, some number of current sources 150 are associated with a particular number of electrodes 106. For example, in FIG. 2A, it is seen that N electrodes $E_1$-$E_N$ are supported by N dedicated current sources $150_1$-$150_N$. In this example, and as is known, the current sources 150 are programmable (programming signals not shown) to provide a current of a certain magnitude and polarity to provide a particular therapeutic current to the patient. For example, if source $150_2$ is programmed to source a 5 mA current, and source $150_3$ is programmed to sink a 5 mA current, then 5 mA of current would flow from anode $E_2$ to cathode $E_3$ through the patient's tissue, R, hopefully with good therapeutic effect. Typically such current is allowed to flow for a duration, thus defining a current pulse, and such current pulses are typically applied to the patient with a given frequency. If the therapeutic effect is not good for the patient, the electrodes chosen for stimulation, the magnitude of the current they provide, their polarities, their durations, or their frequencies could be changed.

(FIG. 2A shows that each of the electrodes is tied to a decoupling capacitor. As is well known, decoupling capacitors promote safety by prevent the direct injection of current form the IPG 100 into the patient. For simplicity, decoupling capacitors are not shown in subsequent drawings, even though they are typically present in practical implementations).

FIG. 2B shows another example current source architecture using a switch matrix 160. In this architecture, the switch matrix 160 is used to route current from any of the sources $150_P$ to any of the electrodes $E_N$. For example, if source $105_2$ is programmed to source a 5 mA current, and source $105_1$ is programmed to sink a 5 mA current, and if source $150_2$ is coupled to electrode E2 by the switch matrix 160, and if source $150_1$ is connected to electrode $E_3$ by the switch matrix 160, then 5 mA of current would flow from anode $E_2$ to cathode $E_3$ through the patient's tissue, R. In this example, because any of the current sources 150 can be connected to any of the electrodes, it is not strictly required that the number of electrodes (N) and the number of current sources (P) be the same. In fact, because it would perhaps be rare to activate all N electrodes at once, it may be sensible to make P less than N, to reduce the number of sources 150 in the IPG architecture. This however may not be the case, and the number of sources and electrodes could be equal (P=N). Although not shown, it should be understood that switch matrix 160 would contains P×N switches, and as many control signals ($C_{1,1}$-$C_{P,N}$), to controllably interconnect all of the sources $150_P$ to any of the N electrodes. Further details of a suitable switch matrix can be found in U.S. Patent Pub. U.S. Patent Publication 2007/0038250, which is incorporated herein by reference.

The architecture of FIG. 2B, like the architecture of FIG. 2A, also comprises some number of current sources 150 (P) associated with a particular number of electrodes 106 (N). Other more complicated current architectures exist in the implantable stimulator art. See, e.g., the above-incorporated '250 Publication. But again generally such approaches all require some number of current sources 150 to be associated with a particular number of electrodes 106.

The inventor considers the association of numbers of current sources and electrodes to be limiting because such architectures do not easily lend themselves to scaling. As implantable stimulator systems become more complicated, greater numbers of electrodes will provide patients more flexible therapeutic options. However, as the number of electrodes grows, so too must the number of current sources according to traditional approaches discussed above. This is considered undesirable by the inventor, because current source circuitry—even when embodied on an integrated circuit—is relatively large and complicated. Newer architectural approaches are thus believed necessary by the inventor to enable the growth of more complicated implantable stimulator systems, and such new architectures are presented herein.

DETAILED DESCRIPTION

Figure 3:
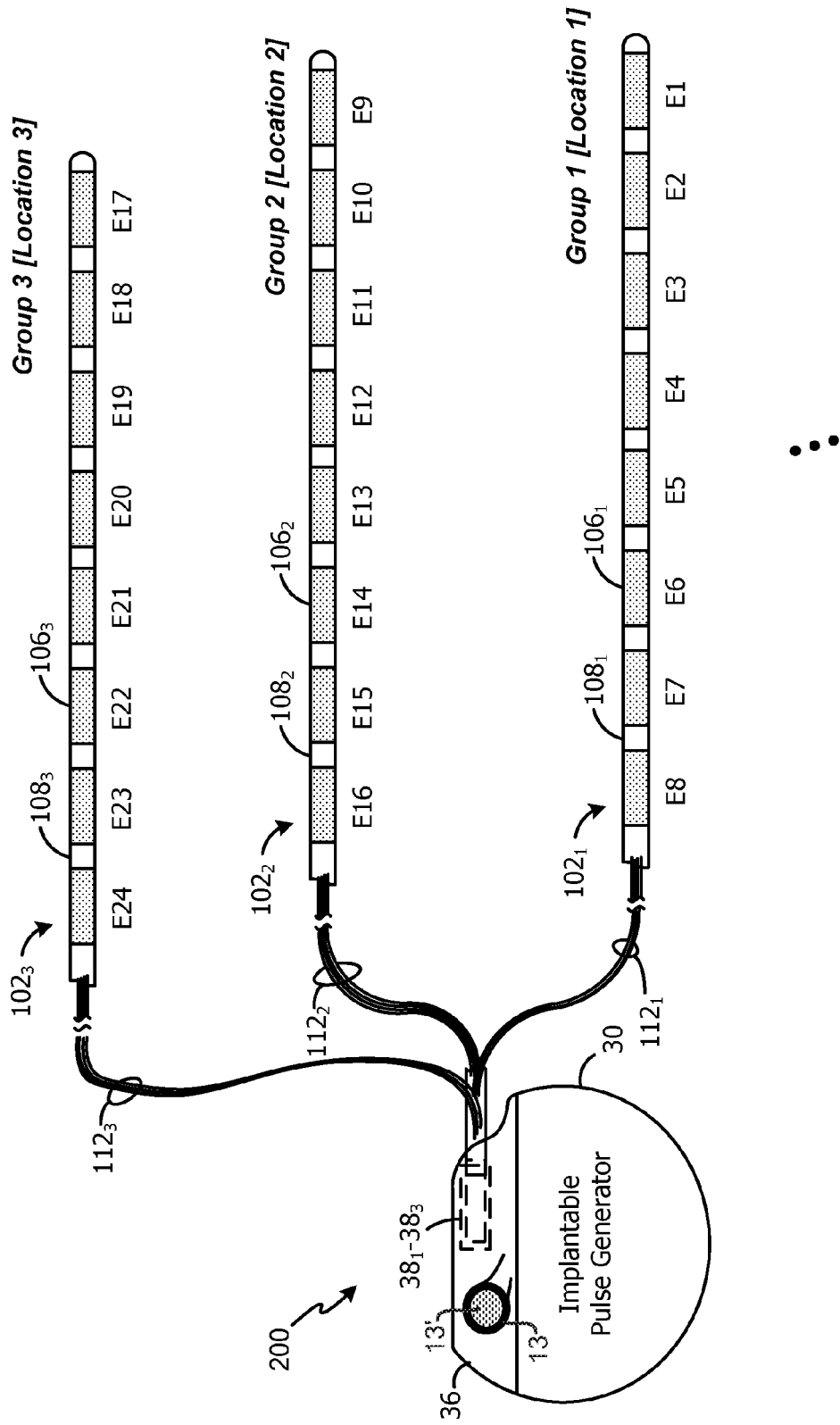
FIG. 3 shows an IPG in accordance with an embodiment of the invention in which a plurality of electrodes are grouped and provided at different locations in a patient.

FIG. 3 shows a more complicated IPG 200 which contains a higher number of electrodes than that illustrated earlier, and which may be indicative of the future progress of IPG technology. In the example shown, there are three electrode arrays $102_1$-$102_3$, each containing eight electrodes, with electrodes $E_1$-$E_8$ on array $102_1$, $E_9$-$E_{16}$ on array $102_2$, and $E_{17}$-$E_{24}$ on array $102_3$. Each of the arrays 102 couples to the IPG 200 at a suitable lead connector $38_1$-$38_3$, which lead connectors can be arranged in the header 36 in any convenient fashion. It should be understood that this is merely an example, and that different numbers of arrays, and different numbers of electrodes on each array, could be used.

In this example, each of the arrays $102_1$-$102_3$ comprises a group of electrodes that is implanted (or implantable) in a different location in a patient's body, thus allowing for the provision of complex stimulation patterns and/or stimulation across a wider portion of the patient's body. For example, in a therapy designed to alleviate sciatica, Location 1 for the Group 1 electrodes of array $102_1$ ($E_1$-$E_8$) might comprise the patient's right leg; Location 2 for the Group 2 electrodes of array $102_2$ ($E_9$-$E_{16}$) the left leg; and Location 3 for the Group 3 electrodes of array $102_3$ ($E_{17}$-$E_{24}$) the patient's spinal column. In a therapy designed to alleviate lower back pain, Location 1 of Group 1 might comprise the right side of a patient's spinal column; Location 2 of Group 2 the left side of the spinal column; and Location 3 of Group 3 a central location in the spinal column. Or each of Locations 1-3 may comprise different portions of a patient's brain in a deep brain stimulation example. The exact locations of each of the arrays, the number of electrodes in each array, and the particular therapies they provide, are not important to the concepts discussed herein. It is preferred that the Locations are non-overlapping in the patient's body.

As discussed in the Background section, conventional wisdom suggests that tripling the number of electrodes (from eight to 24 in this example) would require tripling the number of current sources in the IPG 200 used to support those electrodes. This is because conventional approaches associate a number of current sources with a particular number of electrodes, and hence the two would scale. As noted earlier, the inventor finds this unfortunate given the complexity and size of typical current course circuitry.

Figure 1A:
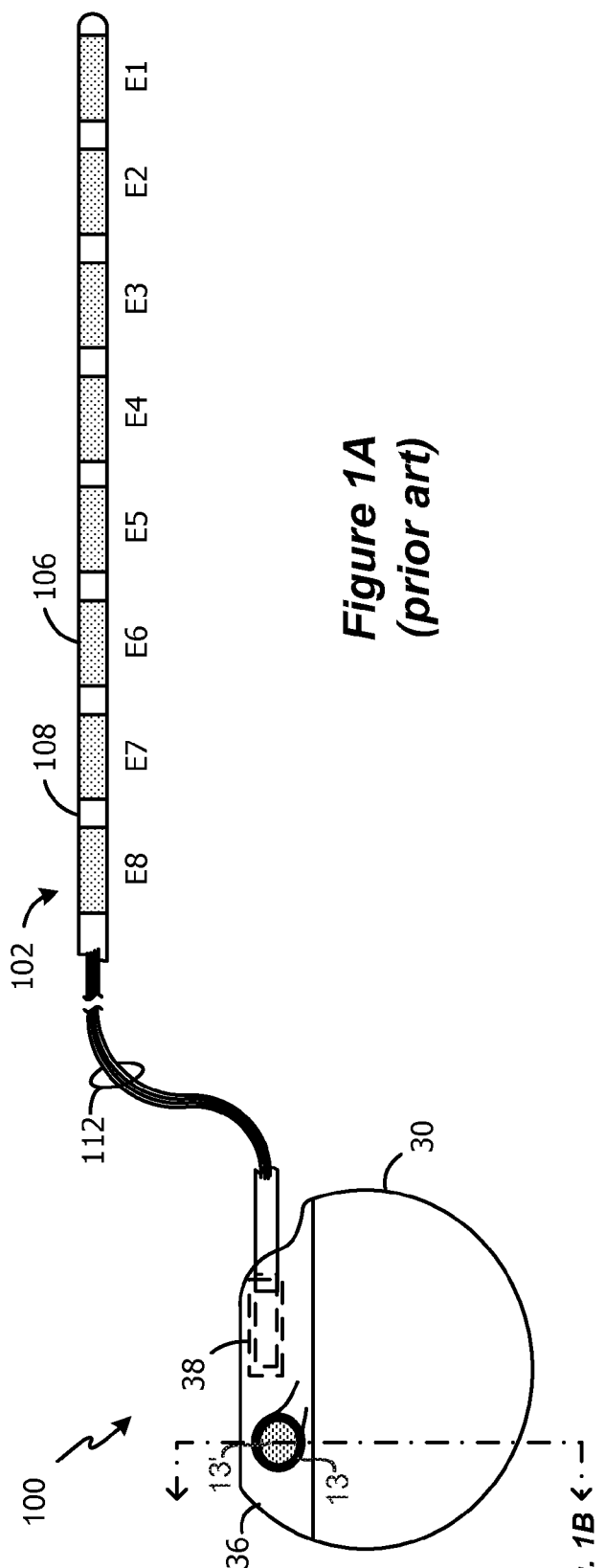
FIGS. 1A and 1B show an implantable pulse generator (IPG), and the manner in which an electrode array is coupled to the IPG in accordance with the prior art.
Figure 1B:
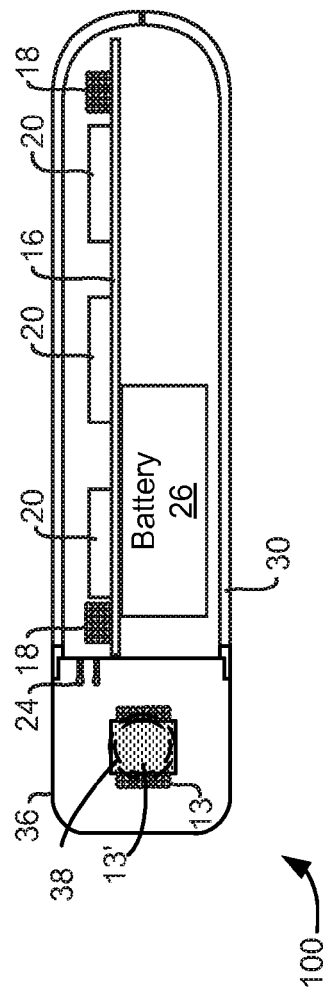
Figure 2A:
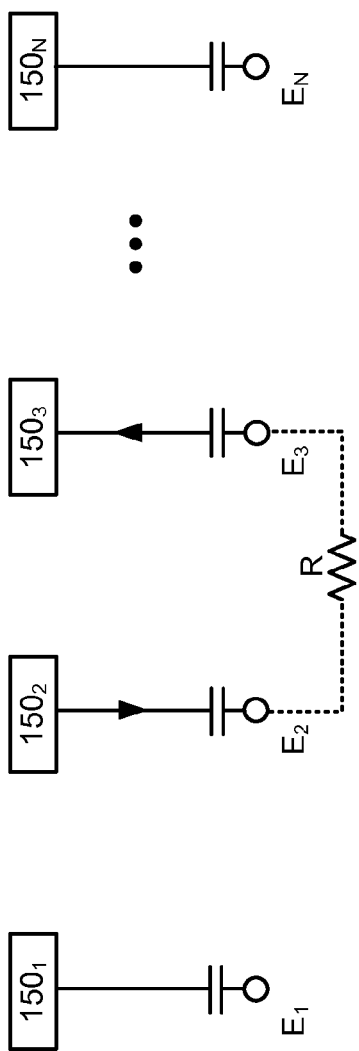
FIGS. 2A and 2B show traditional current source architectures for an IPG in accordance with the prior art.
Figure 4A:
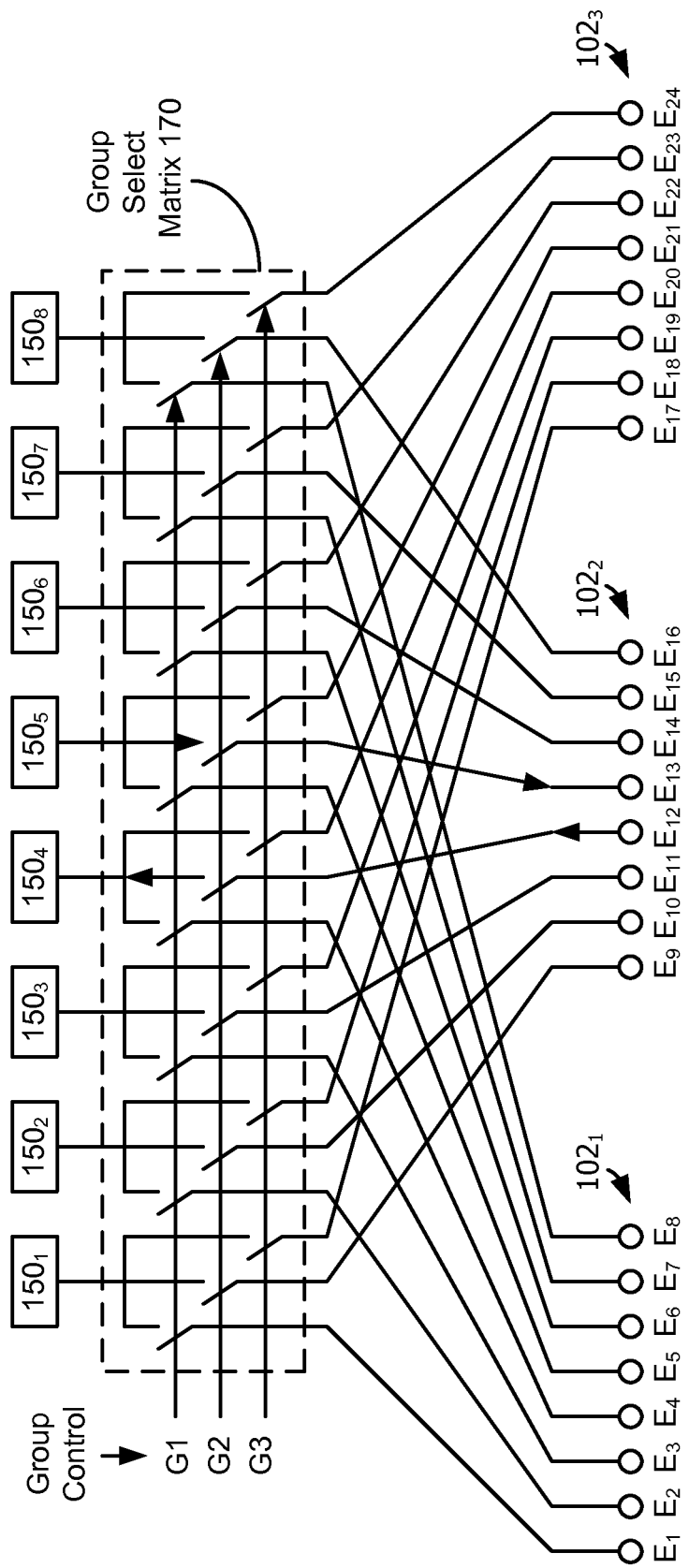
FIGS. 4A and 4B show different current source architectures in accordance with embodiments of the invention to support the IPG of FIG. 3.

The present current source architecture diverges from this conventional approach by sharing current sources with an increased number of electrodes, such as is shown first in FIG. 4A. Consistent with FIG. 3, 24 total electrodes are supported by the current source circuitry of FIG. 4A, comprising three arrays $102_1$-$102_3$ (e.g., Groups) present in three different Locations in the body. FIG. 4A is somewhat similar to the architecture of FIG. 2A discussed earlier, in that there is a one-to-one correspondence of current sources 150 to electrodes within a given Group. For example, there are eight current sources 150, and eight electrodes in each Group. New to FIG. 4A is a group select matrix 170. The group select matrix 170 allows current from the current sources 150 to be sent to particular electrodes in each of the Groups. For example, current source $150_1$ can send its current to electrode $E_1$ in Group 1, to $E_9$ in Group 2, and to $E_{17}$ in Group 3. Current source $150_2$ can send its current to $E_2$ in Group 1, to $E_{10}$ in Group 2, and $E_{18}$ in Group 3, etc.

Group control is enabled in this example by the use of three group control signals G1-G3. When G1 is asserted, switches (e.g., transistors) in the group switch matrix 170 are closed to respectively route the current from each of the current sources $150_1$-$150_8$ to Group 1 electrodes $E_1$-$E_8$. (Of course, not all of the current sources $150_1$-$150_8$ may be programmed at a given moment to provide a current, and so current will not necessarily flow at an electrode $E_1$-$E_8$ merely because of the assertion of G1). When G2 is asserted, each of the current sources $150_1$-$150_8$ are coupled to Group 2 electrodes $E_9$-$E_{16}$, and likewise when G3 is asserted, each of the current sources $150_1$-$150_8$ are coupled to Group 3 electrodes $E_{17}$-$E_{24}$. Although shown as switches, it should be understood that the group switch matrix 170 may also comprise a plurality of multiplexers.

Assume electrode $E_{13}$ is to output 5 mA of current while electrode $E_{12}$ is to receive that 5 mA of current. In this example, source $150_5$ is programmed to source 5 mA worth of current, source $150_4$ is programmed to sink 5 mA of current, and group control signal G2 is asserted.

With this architecture, there is no need to scale the number of current sources; for example, the number of current sources 150 in this example equals eight, even though 24 electrodes are supported. A fourth group of electrodes (e.g., $E_{25}$-$E_{32}$) could also be supported by these same eight current sources, etc. This is of great benefit, and conserves current source resources with the IPG 200.

Figure 2B:
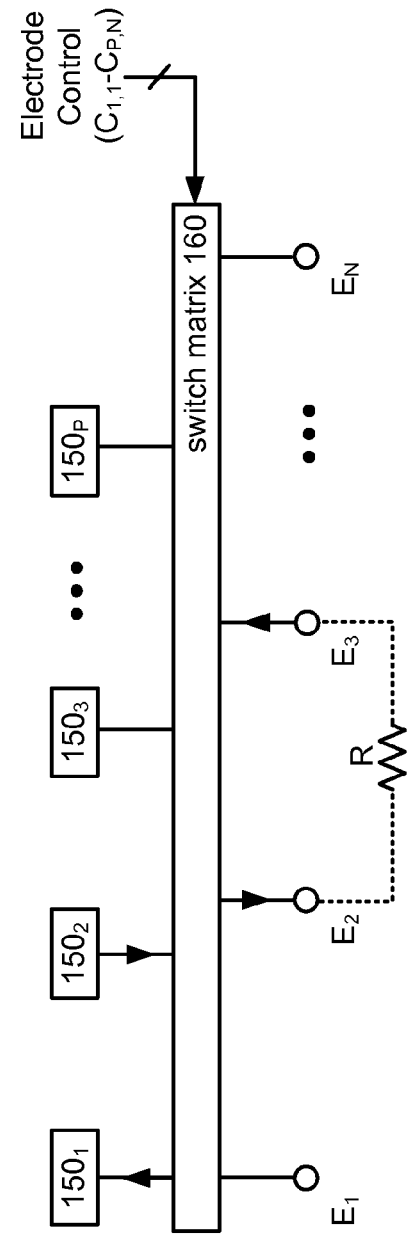
Figure 4B:
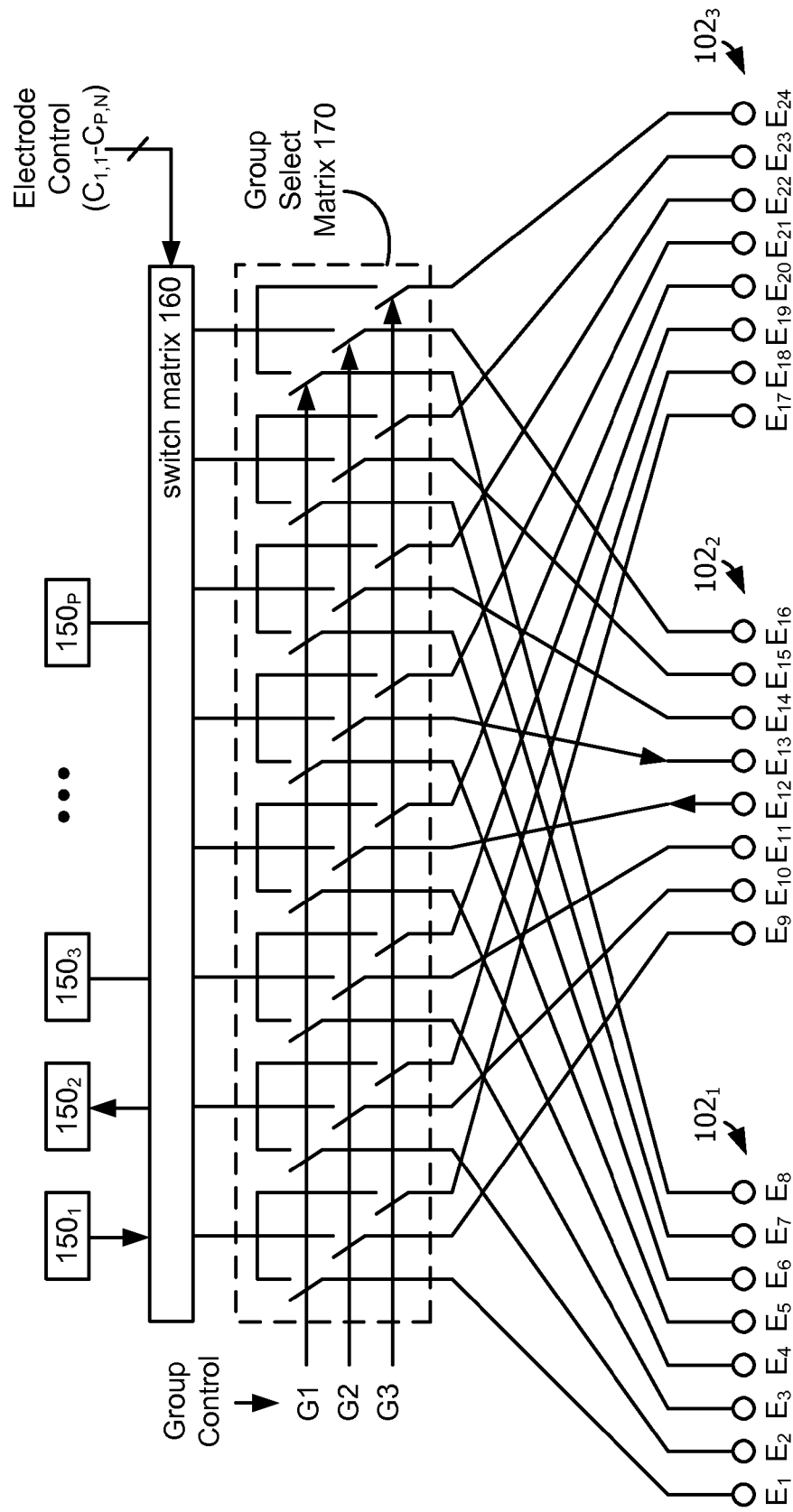

FIG. 4B shows another current source architecture employing a group select matrix 170. The architecture of FIG. 4B is somewhat similar to the architecture of FIG. 2B discussed earlier in that it uses a switch matrix 160 to associate P current sources $150_1$-$150_P$ with a number of switch matrix outputs equal to the number of electrodes (N=8) in each Group. The switch matrix 160 thus allows the current of any of the current sources $150_1$-$150_P$ to be presented at any of the switch matrix 160 outputs, and the group select matrix 170 then routes those outputs to particular electrodes in the selected group.

Assume again that electrode $E_{13}$ is to output 5 mA of current while electrode $E_{12}$ is to receive that 5 mA of current. In this example, any of the P sources can be chosen to source and sink the current; assume that source $150_1$ will source the current, while source $150_2$ will sink the current. Electrode control signals $C_{1,5}$ and $C_{2,4}$ are asserted to close the necessary switches (not shown) in the switch matrix 160 to respectively connect source $150_1$ to the fifth switch matrix output, and source $150_2$ to the fourth switch matrix output. Then group control signal G2 is asserted to respectively route those switch matrix outputs to electrodes $E_{13}$ and $E_{12}$.

Figure 5:
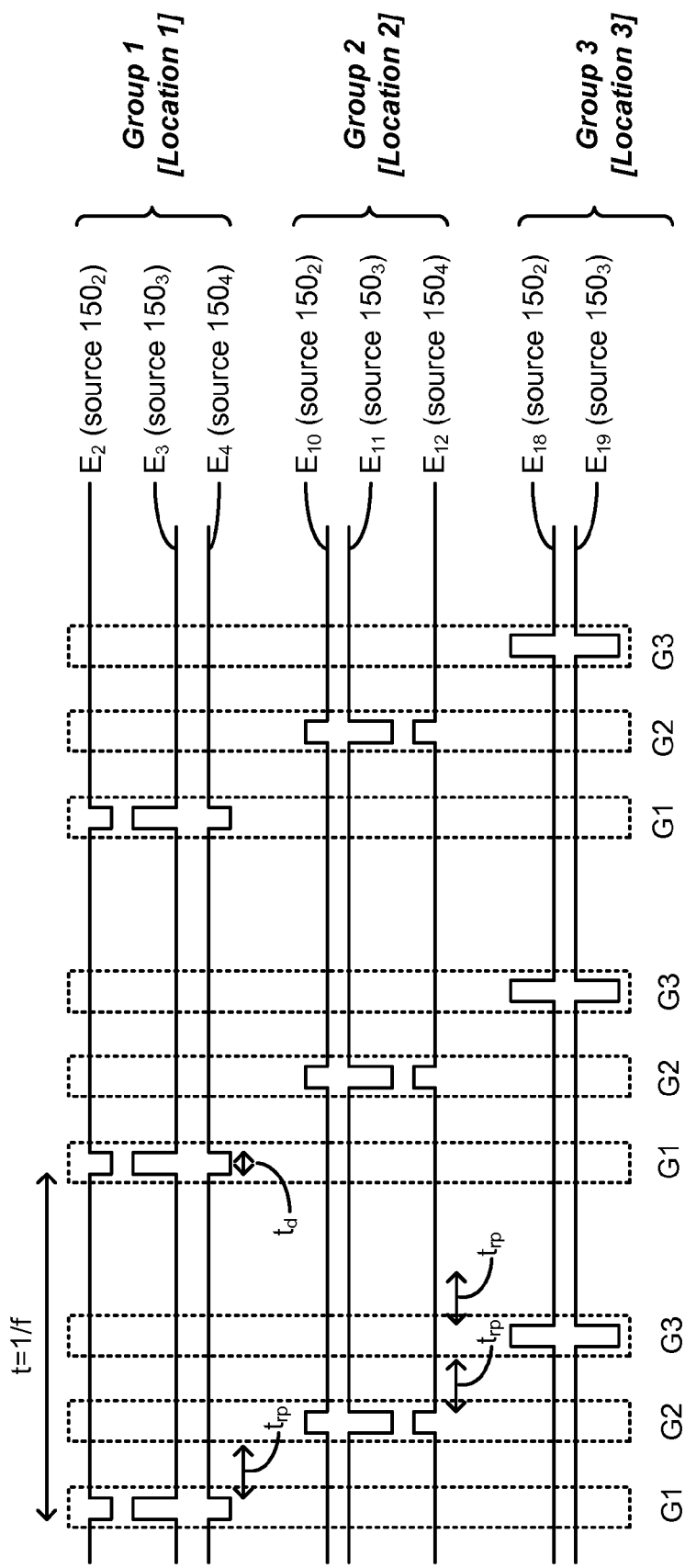
FIGS. 5, 6A and 6B show timing diagrams for operating the IPG of FIG. 3.

FIG. 5 shows examples of therapies that can be enabled using the current source architectures of FIG. 4A or 4B. As before, three arrays of electrodes, defining three Groups, are used to provide therapy to three different Locations in the patient. Assume that the therapies appropriate at each of these Locations have already been determined. For example, assume that at Location 1 it has been determined to source current from electrode $E_3$ and to sink that current from electrodes $E_2$ and $E_4$, and to do so at particular magnitudes and durations $t_d$ which are unimportant for purposes of this example. Assume further that such therapy is to be provided at a frequency of f as shown. Assume further that at Location 2 it has been determined to sink current from electrode $E_{11}$ and to source that current from electrodes $E_{10}$ and $E_{12}$, again at a frequency of f. Assume still further that at Location 3 it has been determined to source current from electrode $E_{18}$ and to sink that current from electrode $E_{19}$, again at a frequency of f.

If the architecture of FIG. 4A is used, such therapy can be delivered as shown in FIG. 5. As shown, the therapies at each of the Locations are interleaved, so that the various therapies are non-overlapping. This allows the current sources 150 to be shared and activated in a time-multiplexed fashion, first being dedicated to provision of therapy at Location 1, then Location 2, then Location 3, and back to Location 1 again, etc. Assume that the architecture of FIG. 4A is used, in which there is a one-to-one correspondence of current sources $150_1$-$150_8$ to electrodes within a given Group, i.e., at a particular Location. In this instance, current sources $150_2$-$150_4$ are used to provide the therapy to electrodes $E_2$-$E_4$ in Group 1/Location1. Notice that group control signal G1 is asserted during this time as shown in FIG. 5. Then later, for example, after a recovery period t as discussed further below, these same current sources $150_2$-$150_4$ are used to provide therapy to electrodes $E_{10}$-$E_{12}$ in Group 2/Location 2, but this time with group control signal G2 asserted. Again after another recovery period, two of these three same current sources $150_2$-$150_3$ are used to provide the therapy to electrodes $E_{18}$ and $E_{19}$ in Group 3/Location 3, but this time with group control signal G3 asserted. To summarize, by interleaving the therapy pulses at the different Groups/Locations, the current sources 150 can be shared and do not have to be increased in number to support the increased number of electrodes.

As is well known, stimulation pulses such as those shown in FIG. 5 would normally be followed by pulses of opposite polarity at the activated electrodes, and even thereafter additional steps may be taken to reduce the build-up of injected charge or to prepare for the provision of the next stimulation pulse. Such portions of time may be referred to generally as a recovery phase, and are shown in FIG. 5 as taking place during a time period $t_{rp}$. It is preferable to not issue a next stimulation pulse until the preceding recovery phase is completed. The details of what occurs during the recovery phases are not shown in FIG. 5 for simplicity.

The extent to which therapies at different Locations can be interleaved will depend on several factors, such as the frequency f of simulation, the duration of the stimulation pulses $t_d$, and the duration of the recovery periods $t_{rp}$. For interleaving and sharing of current sources to occur as shown, these various timing periods should not be in conflict so that access to the current sources can be time multiplexed.

Figure 6A:
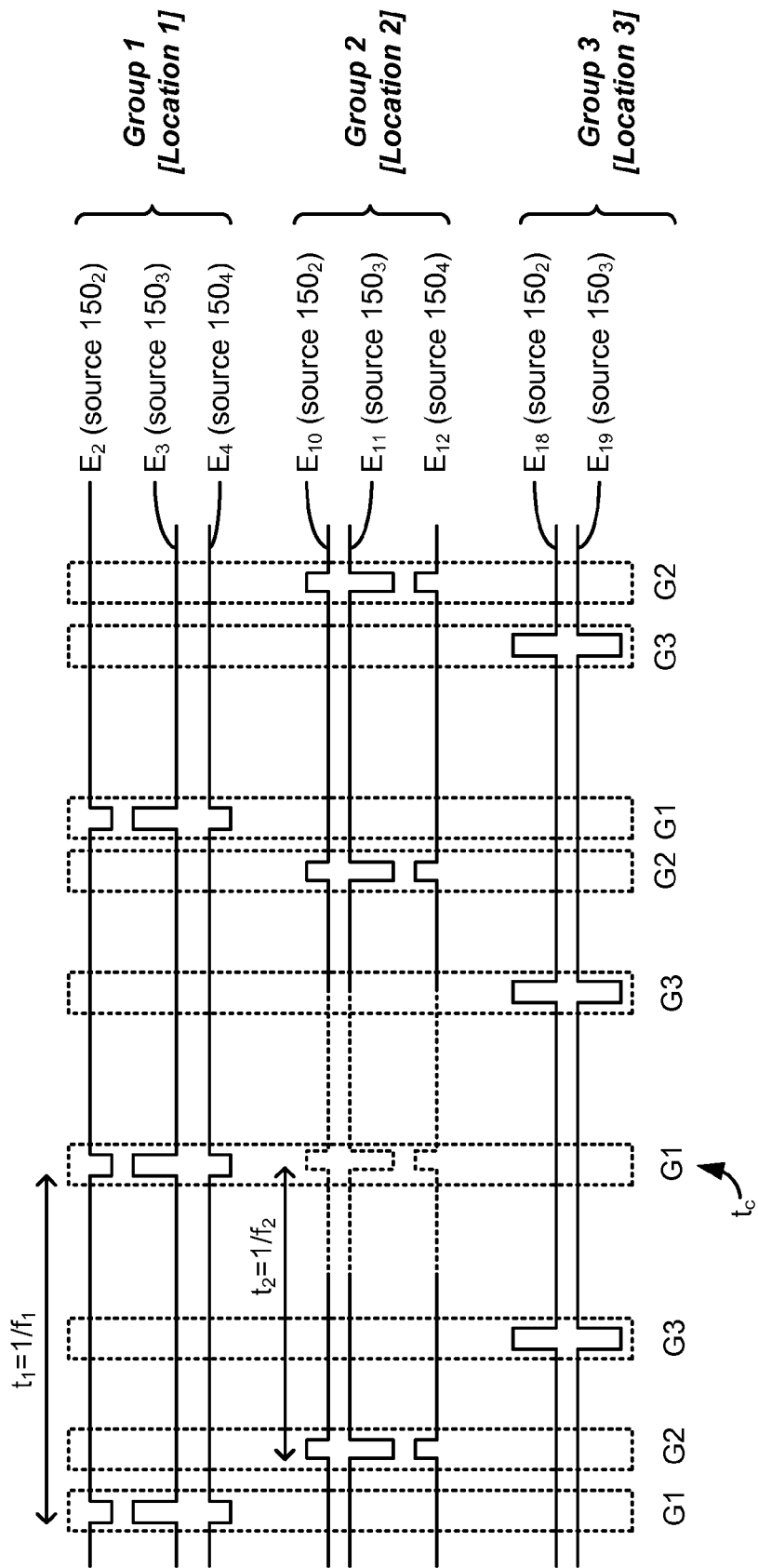

That being said, modifications can be made in the disclosed technique to accommodate at least some potential conflicts. For example, as shown in FIG. 6A, it is seen that the frequency of the therapy provided to the electrodes in Group 2/Location 2 is different ($f_2$) from the frequency provided at the electrodes in Group 1/Location 1 and Group 3/Location 3 ($f_1$). This at times crates periods of conflict, $t_c$, where the Group 2/Location 2 stimulation may overlap with stimulation in other Groups/Locations. For example, specifically shown in FIG. 6A is a conflict between Group 2/Location 2 and Group 1/Location 1, where both of these Groups/Location would be calling for support from the same current sources $150_2$-$150_4$. In this circumstance, and assuming the conflict would not occur too often, the logic 250 in the IPG 200 (discussed below with reference to FIG. 7) may decide to arbitrate the conflict by allowing only the Group 1/Location 1 electrodes access to the desired current sources $150_2$-$150_4$. In other words, the Group 2/Location 2 electrodes would simply not be pulsed during the conflict, as represented by dotted lies in FIG. 6A. Again, assuming such conflicts will not occur frequently, occasionally missing a stimulation pulse at a Group/Location should not materially affect patient therapy. Also, the downside to such therapy gaps can be alleviated by alternating the Groups/Locations being allowed access to the current sources during a conflict, e.g., by enabling Group 1/Location 1 at a first instance of conflict, Group 2/Location 2 at a second instance of conflict, Group 1/Location 1 at a third instance of conflict, etc.

Figure 6B:
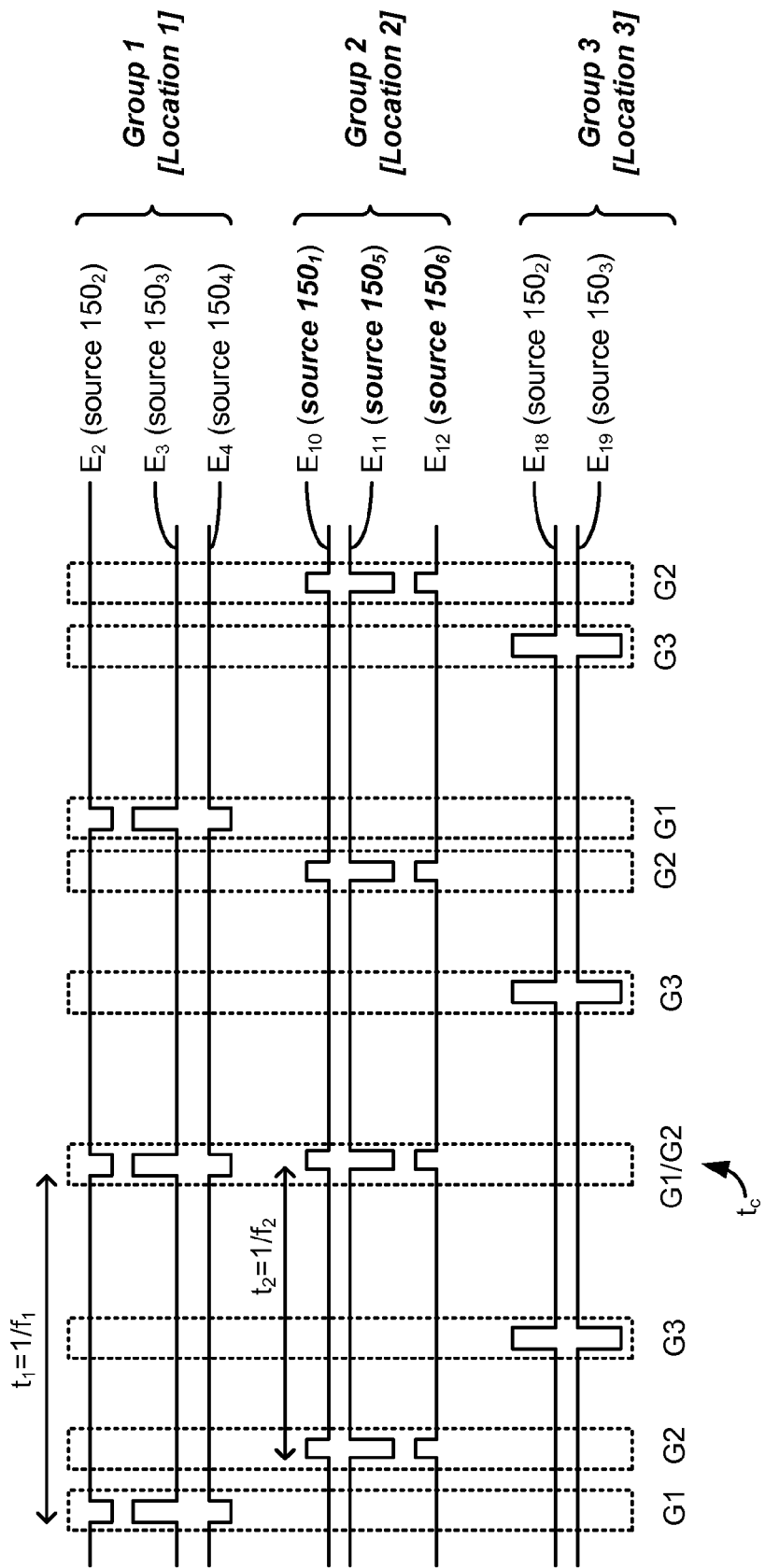

Conflicts of this type can also be resolved in different ways depending on the current source architecture used. FIG. 6B shows the same conflict between Group 1/Location 1 and Group 2/Location 2 presented in FIG. 6A. However, here the logic 250 in the IPG resolves the conflict not by sharing current sources, but instead providing different current sources to Group 1/Location 1 and Group 2/Location 2. Of course, this assumes a more flexible architecture is used in which current sources can be freely assigned to particular electrodes, such as the architecture of FIG. 4B employing a switch matrix 160. Recognizing the conflict, the logic 250 assigns current sources $150_1$, $150_5$, and $150_6$ to electrodes $E_{10}$, $E_{11}$, and $E_{12}$ in Group 2/Location 2, rather than the current sources that might otherwise be expected (i.e., sources $150_2$-$150_4$) which are instead assigned to the electrodes in Group 1/Location 1. Note that during the conflict both group control signals G1 and G2 can be asserted. Note also that current sources $150_2$-$150_3$ are also assigned to the electrodes in Group 3/Location 3, which is possible because there is no conflict between Group 1/Location 1 and Group 3/Location 3.

Figure 7:
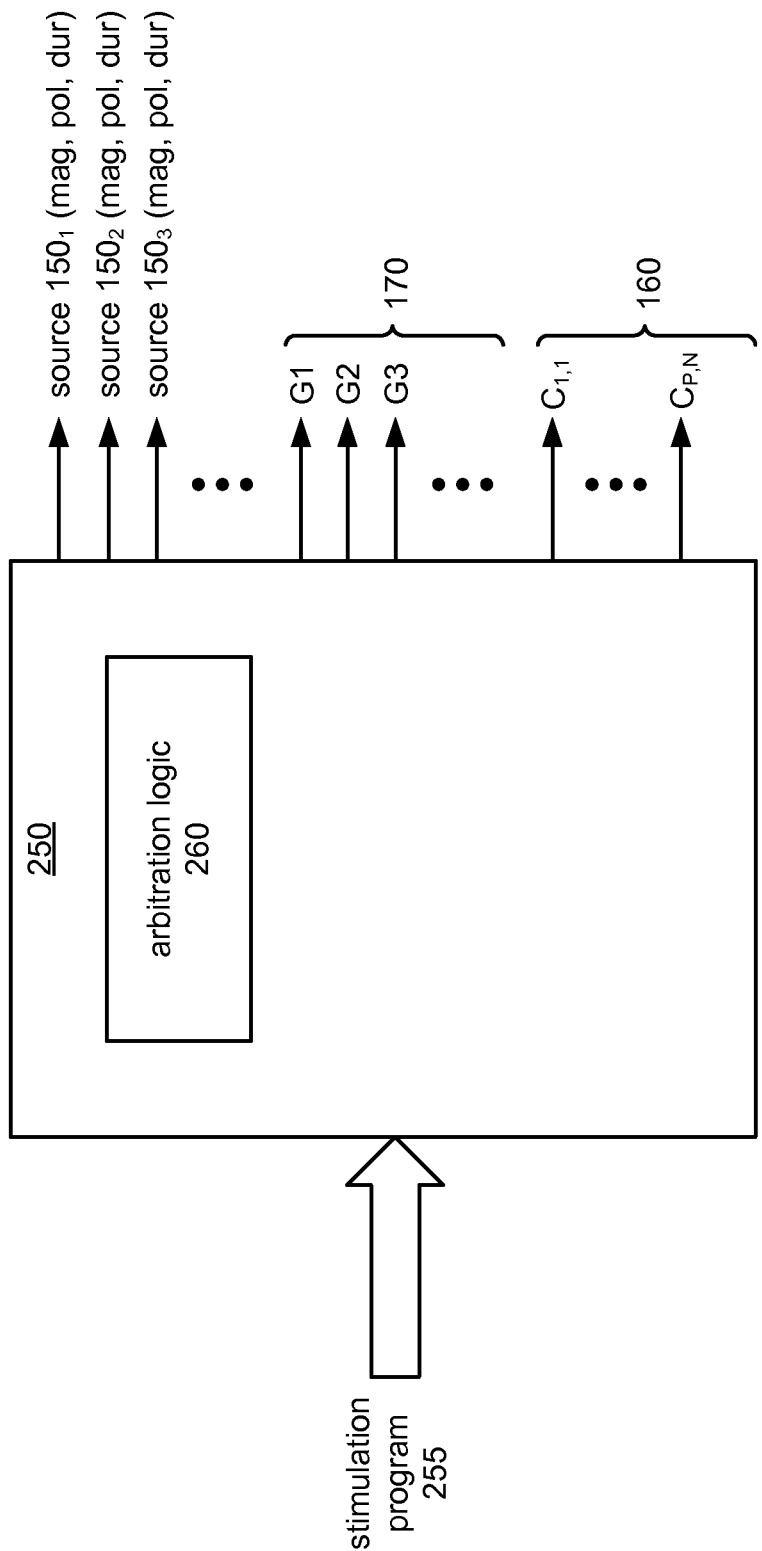
FIG. 7 shows logic for enabling the current source architectures described herein.

As noted above, control of the various current source architectures disclosed herein can be achieved by suitably programmed logic circuitry 250, as shown in FIG. 7. Logic 250 in one example can comprise a microcontroller, as is common in an IPG. While the microcontroller 250 can implement many different IPG functions, as relevant here the microcontroller is responsible for processing one or more stimulation programs 255 dictating therapy for a patient, and for enabling the current sources and groups accordingly. In one embodiment, the stimulation program 255 comprises separate stimulation programs for each Group/Location, which specific programs may have been arrived at through a fitting procedure during which the patient expresses his preference for particular settings. As shown, the microcontroller 250 ultimately issues commands to the current source architecture at appropriate times, including enabling particular current sources 150, and specifying the magnitude, polarity, and duration of the current pulses. Also ultimately issued by the microcontroller 250 are the group control signals (G1, G2, etc.), which are received at the group select matrix 170. If the current source architecture employs a switching matrix 160 as shown and described in FIG. 4B for example, the microcontroller 250 can also issue the control signals for that matrix ($C_{1,1}$-$C_{P,N}$). To the extent that the stimulation program 255 presents a conflict, such as those discussed earlier with respect to FIGS. 6A and 6B, special arbitration logic 260 may be used to resolve the conflict, such as by skipping certain stimulation pulses (FIG. 6A), rerouting alternative current sources 150 if possible (FIG. 6B), or in other ways.

Figure 8A:
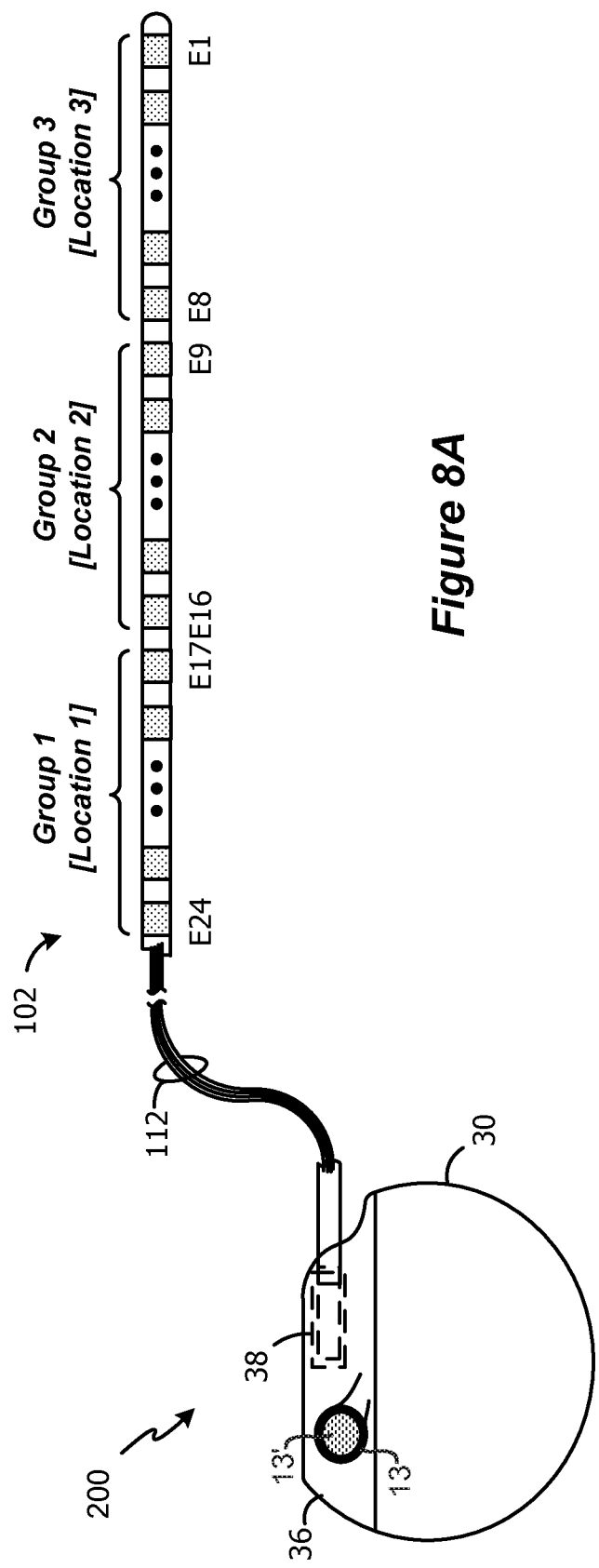
FIGS. 8A and 8B show alternative arrangements for grouping of electrodes in an IPG in accordance with embodiments of the invention.
Figure 8B:
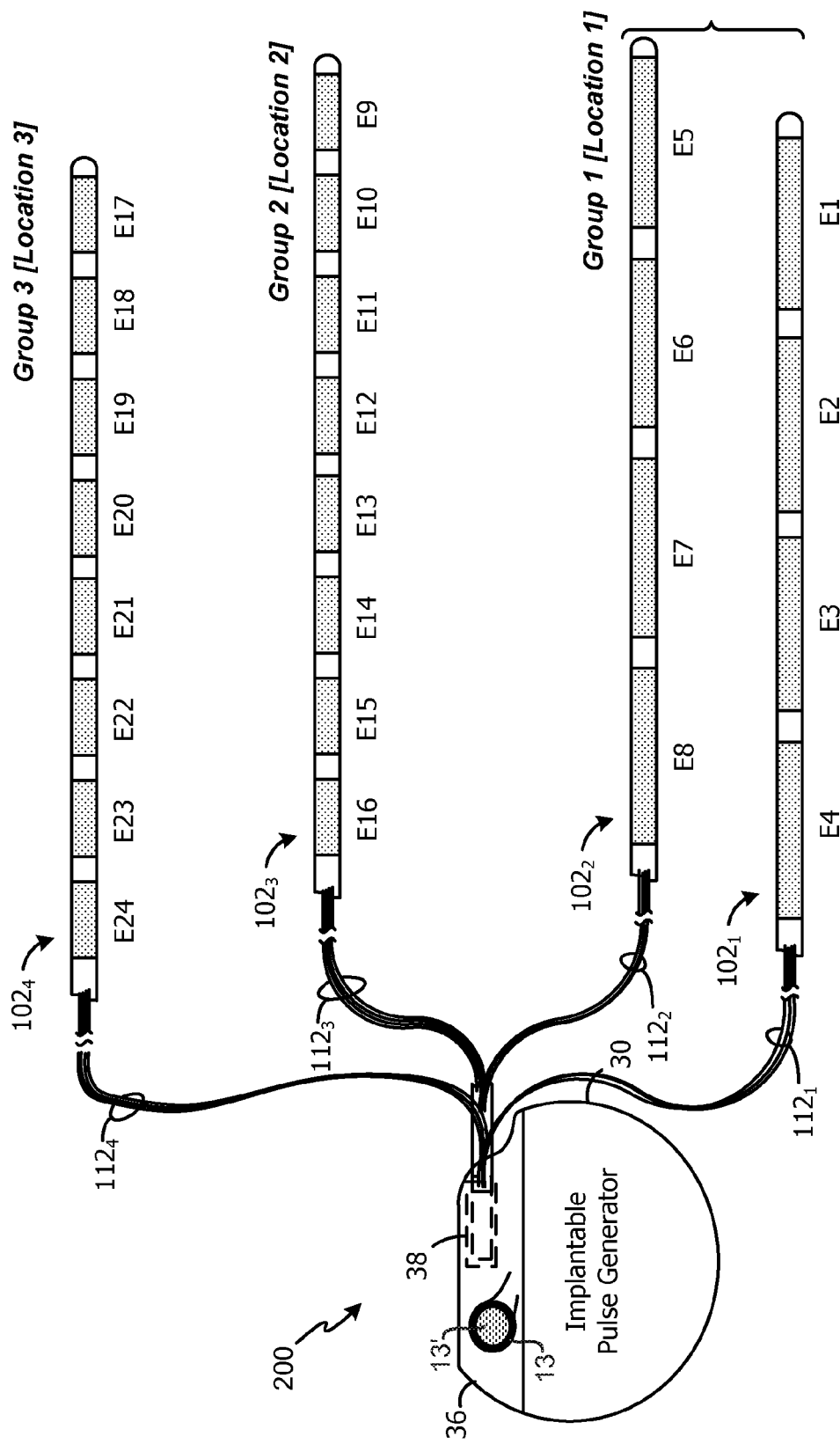

To this point it has been assumed that Groups/Locations of electrodes correspond to particular arrays 102 coupled to the IPG. But this is not necessarily the case, and groups of electrodes and their locations can be established in other ways. For example, FIG. 8A shows a single electrode arrays having 24 electrodes, divided into three Groups of eight. Each of these Groups corresponds to a different Location for therapy, even though present on the same array 102, and thus this type of electrode grouping arrangement can still benefit from the current source architectures described herein. For example, eight current sources 150 can be employed if the architecture of FIG. 4A is used, or P current sources if the architecture of FIG. 4B is used. FIG. 8B shows another example in which a plurality of arrays ($102_1$ and $102_2$) are treated as one Group of eight electrodes, even though such arrays would not be at exactly the same location in the patient. Nonetheless, the 24 electrodes present in FIG. 8B can be supported by eight current sources (FIG. 4A) or P current sources (FIG. 4B).

It should be understood that a "current source" comprises any type of power source capable of delivering a stimulation current to an electrode, such as a constant current source, a constant voltage source, or combinations of such sources.

A "microcontroller" should be understood as any suitable logic circuit, whether integrated or not, or whether implemented in hardware or software.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable stimulator device, comprising:
a plurality of groups each comprising a plurality of electrodes;
a plurality of current sources;
a switch matrix controllable by a plurality of first control signals for coupling each of the current sources to any of a plurality of switch matrix outputs; and
a group selection matrix controllable by at least one group control signal, wherein each group control signal is configured to simultaneously couple the plurality of switch matrix outputs to a selected group of the plurality of electrodes.

2. The device of claim 1, wherein there are a plurality N of electrodes in each group, and N current sources.

3. The device of claim 1, wherein there are a plurality N of electrodes in each group, and a plurality P of current sources.

4. The device of claim 3, wherein P is less than N.

5. The device of claim 1, further comprising a plurality of arrays each comprising one of the groups of electrodes, wherein each array is implantable at a different location in a patient.

6. The device of claim 1, further comprising an array, wherein all of the groups of electrodes are located on the array.

7. The device of claim 1, further comprising a plurality of arrays, and wherein at least one group of electrodes is located on a plurality of the arrays.

8. The device of claim 1, wherein each group control signal is configured to couple the plurality of switch matrix outputs to only a selected group at a given time.

9. The device of claim 1, wherein the group selection matrix simultaneously couples the plurality of switch matrix outputs to a selected group at a first time and simultaneously couples the plurality of switch matrix outputs to another group at a second time.

10. The device of claim 1, wherein each of the plurality of electrodes in one of the plurality of groups is not in any other of the plurality of groups.

11. The device of claim 1, further comprising a microcontroller.

12. The device of claim 11, wherein there are a plurality X of groups, and wherein the microcontroller is configured to assert the at least one group control signal to simultaneously couple the plurality of switch matrix outputs to each of the X groups at X different times.

13. The device of claim 11, wherein there are a plurality X of groups, and wherein the microcontroller is configured to assert each of the X group control signals at X different times to simultaneously couple the plurality of switch matrix outputs to each of the X groups at the X different times.

14. The device of claim 11, wherein the microcontroller receives at least one stimulation program and is configured to enable the at least one group control signal and the first control signals for the switch matrix in accordance with the at least one stimulation program.

* * * * *